United States Patent
Baetscher

(12)
(10) Patent No.: US 6,670,151 B1
(45) Date of Patent: *Dec. 30, 2003

(54) PORCINE STEM CELL FACTOR VARIENTS AND RECOMBINANT CELLS EXPRESSING SUCH POLYPEPTIDES

(75) Inventor: Manfred Baetscher, Portland, OR (US)

(73) Assignee: BioTransplant, Inc., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/485,639

(22) PCT Filed: Aug. 13, 1998

(86) PCT No.: PCT/US98/16843

§ 371 (c)(1),
(2), (4) Date: Apr. 25, 2000

(87) PCT Pub. No.: WO99/09163

PCT Pub. Date: Feb. 25, 1999

Related U.S. Application Data

(60) Provisional application No. 60/055,735, filed on Aug. 13, 1997.

(51) Int. Cl.[7] .......................... C12P 21/02; C12N 15/63; C12N 1/21; C12N 5/10; C07H 21/04

(52) U.S. Cl. ...................... 435/69.5; 435/357; 435/325; 435/252.3; 435/320.1; 530/350; 536/23.5

(58) Field of Search ................................ 435/69.5, 354, 435/357, 325, 252.3, 320.1; 530/350; 536/23.5

(56) References Cited

U.S. PATENT DOCUMENTS 5,453,357 A * 9/1995 Hogan ........................ 435/7.21
5,589,582 A * 12/1996 Hawley et al. ............. 536/23.5

FOREIGN PATENT DOCUMENTS

WO    WO 94/09803    5/1994

OTHER PUBLICATIONS

Zhang et al. Porcine stem cell factor/c–kit ligand: its molecular cloning and localization within the uterus. Biol. Reprod. Jan. 1994;50(1):95–102.*

Greenwood et al. Cloning, sequencing and expression of stem cell factor (c–kit ligand) cDNA of brushtail possum (*Trichosurus vulpecula*). Reproduction, Fertility, and Development, (1996) 8 (4) 789–95.*

Matsui et al. Derivation of pluripotential embryonic stem cells from murine primordial germ cells in culture. Cell. 1992 Sep. 4;70(5):841–7.*

Bowie et al. Deciphering the message in protein sequences: tolerance to amino acid substitutions. Science, (Mar. 16, 1990) 247 (4948) 1306–10.*

Ngo et al., in The Protein Folding Problem and Tertiary Structure Prediction, Merz and Le Grand (Eds), Aug. 1994, Springer Verlag, pp. 433 and 492–495.*

XP 002084191, Anderson, et al., "Molecular Cloning of Mast Cell Growth Factor, a Hematopoietin That Is Active in Both Membrane Bound and Soluble Forms", vol. 63, pp. 235–243 (1990).

* cited by examiner

*Primary Examiner*—David Romeo
(74) *Attorney, Agent, or Firm*—Elliot M. Olstein; Alan J. Grant

(57) ABSTRACT

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been identified as porcine stem cell factors, and in particular membrane-bound porcine stem cell factors, and still more particularly as being involved in the culture of pluripotent or totipotent porcine cells.

7 Claims, 7 Drawing Sheets

FIG. 1A

```
GAGCTCCAGA ACAGGTAAAC GGAGTTGCCA CACCGCTGCC TGGGCTGGAT CACAGCGCTG    60
CCTTTCCTT ATG AAG AAG ACA CAA ACT TGG ATT ATC ACT TGC ATT TAT       108
          Met Lys Lys Thr Gln Thr Trp Ile Ile Thr Cys Ile Tyr
          -25                 -20                 -15

CTT CAA CTG CTC CTA TTT AAT CCT CTC GTC AGA ACT CAA GGG ATC TGC     156
Leu Gln Leu Leu Leu Phe Asn Pro Leu Val Arg Thr Gln Gly Ile Cys
        -10                  -5                   1

AGG AAC CGT GTG ACT GAT GAT GTG AAA GAC GTT ACA AAA TTG GTG GCA     204
Arg Asn Arg Val Thr Asp Asp Val Lys Asp Val Thr Lys Leu Val Ala
 5                  10                  15                  20

AAT CTT CCA AAA GAC TAT AAG ATA ACC CTC AAA TAT GTC CCC GGG ATG     252
Asn Leu Pro Lys Asp Tyr Lys Ile Thr Leu Lys Tyr Val Pro Gly Met
             25                  30                  35

GAC GTT TTG CCT AGT CAT TGT TGG ATA AGC GAA ATG GTG GAA CAA CTG     300
Asp Val Leu Pro Ser His Cys Trp Ile Ser Glu Met Val Glu Gln Leu
 40                  45                  50

TCA GTC AGC TTG ACT GAT CTT CTG GAC AAG TTT TCC AAT ATT TCT GAA     348
Ser Val Ser Leu Thr Asp Leu Leu Asp Lys Phe Ser Asn Ile Ser Glu
         55                  60                  65

GGC TTG AGT AAT TAT TCT ATC ATA GAC AAA CTT GTG CTT AAA ATT GAT     396
Gly Leu Ser Asn Tyr Ser Ile Ile Asp Lys Leu Val Leu Lys Ile Asp
                 70                  75                  80

GAC CTC GTG GAA TGC ATG GAA GAA CAC TCA TTT GAG AAT GTA AGA AAA     444
Asp Leu Val Glu Cys Met Glu Glu His Ser Phe Glu Asn Val Arg Lys
             85                  90                  95                 100

TCA TCT AAG AGC CCA GAA CCC AGG CTG TTT ACT CCT GAA AAA TTC TTT     492
Ser Ser Lys Ser Pro Glu Pro Arg Leu Phe Thr Pro Glu Lys Phe Phe
                 105                 110                 115
```

FIG. 1B

```
GGG ATT TTT AAT AGA TCC ATC GAT GCC TTC AAG GAT TTG GAG ATG GTG   540
Gly Ile Phe Asn Arg Ser Ile Asp Ala Phe Lys Asp Leu Glu Met Val
        120                 125                 130

GCA CCT AAA ACT AGT GAA TGT GTG ATT TCT TCA ACA TTA ACT CCT GAA   588
Ala Pro Lys Thr Ser Glu Cys Val Ile Ser Ser Thr Leu Thr Pro Glu
        135                 140                 145

AAA GAT TCC AGA GTC AGT GTC ACA AAA TTT ATG CCC CCT GTT   636
Lys Asp Ser Arg Val Ser Val Thr Lys Phe Met Pro Pro Val
        150                 155                 160

GCA GCC TCC CTT AGG AAT GAC AGT AGT AGT AAT AGG AAA GCC   684
Ala Ala Ser Leu Arg Asn Asp Ser Ser Ser Asn Arg Lys Ala
    165                 170                 175         180

TCA GAT TCG ATT GAA GAC TCC AGC CTC CAG TGG GCA GCG GTA GCA TTG   732
Ser Asp Ser Ile Glu Asp Ser Ser Leu Gln Trp Ala Ala Val Ala Leu
        185                 190                 195

CCA GCA TTC TTC CTT GTG ATT GGG TTT GCT TTT GGA GCC TTA TAC   780
Pro Ala Phe Phe Leu Val Ile Gly Phe Ala Phe Gly Ala Leu Tyr
        200                 205                 210

TGG AAG AAG CAA CCA AAC CTT ACA AGG ACA GTG GAA AATAATA GAG   828
Trp Lys Lys Gln Pro Asn Leu Thr Arg Thr Val Glu Asn Ile Gln
        215                 220                 225

ATT AAT GAA GAG GAT AAT GAG ATA AGT ATG TTG CAA GAA AAA GAG AGA   876
Ile Asn Glu Glu Asp Asn Glu Ile Ser Met Leu Gln Glu Lys Glu Arg
        230                 235                 240

GAG TTT CAA GAA GTG TAA TTGTGGCGTG TATCAACACT GTTGCTTTCG TACATTGGGT   934
Glu Phe Gln Glu Val
    245

GGTAACAGTT GATGTTTG   952
```

FIG. 2A

```
                                                                GCGCT GCCTTCCTT      15

ATG AAG ACA CAA ACT TGG ATT ATC ACT TGC ATT TAT CTT CAA CTG                         63
Met Lys Thr Gln Thr Trp Ile Ile Thr Cys Ile Tyr Leu Gln Leu
-25             -20             -15             -10

CTC CTA TTT AAT CCT CTC GTC AGA ACT CAA GGG ATC TGC AGG AAC CGT                    111
Leu Leu Phe Asn Pro Leu Val Arg Thr Gln Gly Ile Cys Arg Asn Arg
            -5               1               5

GTG ACT GAT GAT GTG AAA GAC GTT ACA AAA TTG GTG GCA AAT CTT CCA                    159
Val Thr Asp Asp Val Lys Asp Val Thr Lys Leu Val Ala Asn Leu Pro
        10              15              20

AAA GAC TAT AAG ATA ACC CTC AAA TAT GTC CCC GGG ATG GAC GTT TTG                    207
Lys Asp Tyr Lys Ile Thr Leu Lys Tyr Val Pro Gly Met Asp Val Leu
    25              30              35

CCT AGT CAT TGT TGG ATA AGC GAA ATG GTG GAA CAA CTG TCA GTC AGC                    255
Pro Ser His Cys Trp Ile Ser Glu Met Val Glu Gln Leu Ser Val Ser
40              45              50              55

TTG ACT GAT CTT CTG GAC AAG TTT TCC AAT ATT TCT GAA GGC TTG AGT                    303
Leu Thr Asp Leu Leu Asp Lys Phe Ser Asn Ile Ser Glu Gly Leu Ser
        60              65              70
```

FIG. 2B

```
AAT TAT TCT ATC ATA GAC AAA CTT GTG AAA ATT GTT GAT GAC CTC GTG    351
Asn Tyr Ser Ile Ile Asp Lys Leu Val Lys Ile Val Asp Asp Leu Val
                 75                  80                  85

GAA TGC ATG GAA GAA CAC TCA TTT GAG AAT GTA AGA AAA TCA TCT AAG    399
Glu Cys Met Glu Glu His Ser Phe Glu Asn Val Arg Lys Ser Lys
         90                  95                 100

AGC CCA GAA CCC AGG CTG TTT ACT CCT GAA AAA TTC TTT GGG ATT TTT    447
Ser Pro Glu Pro Arg Leu Phe Thr Pro Glu Lys Phe Phe Gly Ile Phe
        105                 110                 115

AAT AGA TCC ATC GAT GCC TTC AAG GAT TTG GAG ATG GTG GCA CCT AAA    495
Asn Arg Ser Ile Asp Ala Phe Lys Asp Leu Glu Met Val Ala Pro Lys
120                 125                 130                 135

ACT AGT GAA TGT GTG ATT GTG TCT TCA ACA TTA ACT CCT GAA AAA GAT TCC    543
Thr Ser Glu Cys Val Ile Ser Ser Thr Leu Thr Pro Glu Lys Asp Ser
                140                 145                 150

AGA GTC AGT GTC ACA AAA CCA TTA ATG TTT CCC CCT GTT GCA GCC AGC    591
Arg Val Ser Val Thr Lys Pro Leu Met Phe Pro Pro Val Ala Ala Ser
            155                 160                 165

TCC CTT AGG AAT GAC AGC AGT AGC AGT AAT AGG AAA GCC TAA            633
Ser Leu Arg Asn Asp Ser Ser Ser Ser Asn Arg Lys Ala
        170                 175                 180
```

FIG. 4A

| | | | | | | | | | | |
|---|---|---|---|---|---|---|---|---|---|---|
|CGCTGCCTTT|CCTT|ATG<br>Met<br>-25|AAG<br>Lys|AAG<br>Lys|ACA<br>Thr|CAA<br>Gln|ACT<br>Thr<br>-20|TGG<br>Trp|ATT<br>Ile|ATC<br>Ile|ACT<br>Thr<br>-15|TGC<br>Cys|ATT<br>Ile . |50|
|TAT<br>Tyr|CTT<br>Leu|CAA<br>Gln<br>-10|CTG<br>Leu|CTC<br>Leu|CTA<br>Leu|TTT<br>Phe|AAT<br>Asn|CCT<br>Pro<br>-5|CTC<br>Leu|GTC<br>Val|AGA<br>Arg|ACT<br>Thr|CAA<br>Gln<br>1|GGG<br>Gly|ATC<br>Ile|98|
|TGC<br>Cys|AGG<br>Arg<br>5|AAC<br>Asn|CGT<br>Arg|GTG<br>Val|ACT<br>Thr|GAT<br>Asp|GAT<br>Asp<br>10|GTG<br>Val|AAA<br>Lys|GAC<br>Asp|GTT<br>Val|ACA<br>Thr<br>15|AAA<br>Lys|TTG<br>Leu|GTG<br>Val|146|
|GCA<br>Ala|AAT<br>Asn<br>20|CTT<br>Leu|CCA<br>Pro|AAA<br>Lys|TAT<br>Tyr|GAC<br>Asp<br>25|AAG<br>Lys|ATA<br>Ile|ACC<br>Thr|CTC<br>Leu|ACT<br>Thr<br>30|CTC<br>Leu|AAA<br>Lys|TAT<br>Tyr|GTC<br>Val|CCC<br>Pro|GGG<br>Gly<br>35|194|
|ATG<br>Met|GAC<br>Asp|GTT<br>Val<br>40|TTG<br>Leu|CCT<br>Pro|AGT<br>Ser|CAT<br>His|TGT<br>Cys<br>45|TGG<br>Trp|ATA<br>Ile|TCT<br>Ser|AGC<br>Ser|GAA<br>Glu<br>50|ATG<br>Met|GTG<br>Val|GAA<br>Glu|CAA<br>Gln|242|
|CTG<br>Leu|TCA<br>Ser<br>55|GTC<br>Val|AGC<br>Ser|TTG<br>Leu|ACT<br>Thr|GAT<br>Asp<br>60|CTT<br>Leu|CTG<br>Leu|GAC<br>Asp|AAG<br>Lys|TTT<br>Phe<br>65|TCC<br>Ser|AAT<br>Asn|ATT<br>Ile|TCT<br>Ser|290|
|GAA<br>Glu|GGC<br>Gly<br>70|TTG<br>Leu|AGT<br>Ser|AAT<br>Asn|TAT<br>Tyr|TCT<br>Ser<br>75|ATC<br>Ile|ATA<br>Ile|GAC<br>Asp|AAA<br>Lys|CTT<br>Leu<br>80|GTG<br>Val|AAA<br>Lys|ATT<br>Ile|GTT<br>Val|338|
|GAT<br>Asp|GAC<br>Asp<br>85|CTC<br>Leu|GTG<br>Val|GAA<br>Glu|TGC<br>Cys|ATG<br>Met<br>90|GAA<br>Glu|GAA<br>Glu|CAC<br>His|TCA<br>Ser|TTT<br>Phe<br>95|GAG<br>Glu|AAT<br>Asn|GTA<br>Val|AGA<br>Arg|386|

FIG. 4B

| | | | | | | | | | | | |
|---|---|---|---|---|---|---|---|---|---|---|---|
| AAA | TCT | AAG | AGC | CCA | GAA | CCC | AGG | CTG | TTT | ACT | CCT | GAA | AAA | TTC | 434 |
| Lys | Ser | Lys | Ser | Pro | Glu | Pro | Arg | Leu | Phe | Thr | Pro | Glu | Lys | Phe |
| 100 | | | | 105 | | | | | 110 | | | | | 115 |

```
AAA TCT AAG AGC CCA GAA CCC AGG CTG TTT ACT CCT GAA AAA TTC    434
Lys Ser Lys Ser Pro Glu Pro Arg Leu Phe Thr Pro Glu Lys Phe
100             105             110             115

TTT GGG ATT TTT AAT AGA TCC ATC GAT GCC TTC AAG GAT TTG GAG ATG    482
Phe Gly Ile Phe Asn Arg Ser Ile Asp Ala Phe Lys Asp Leu Glu Met
        120             125             130

GTG GCA CCT AAA ACT AGT GAA TGT GTG ATT TCT TCA ACA TTA ACT CCT    530
Val Ala Pro Lys Thr Ser Glu Cys Val Ile Ser Ser Thr Leu Thr Pro
135             140             145

GAA AAA GGG AAT GAC AGC AGT AGC AGT AAT AGG AAA GCC TCA GAT TCG    578
Glu Lys Gly Asn Asp Ser Ser Ser Ser Asn Arg Lys Ala Ser Asp Ser
        150             155             160

ATT GAA GAC TCC AGC CTC CAG TGG GCA GCG GTA GCA TTG CCA GCA TTC    626
Ile Glu Asp Ser Ser Leu Gln Trp Ala Ala Val Ala Leu Pro Ala Phe
165             170             175

TTC TCT CTT GTG ATT GGG TTT GCT TTT GGA GCC TTA TAC TGG AAG AAG    674
Phe Ser Leu Val Ile Gly Phe Ala Phe Gly Ala Leu Tyr Trp Lys Lys
180             185             190             195

AAA CAA CCA AAC CTT ACA AGG ACA GTG GAA AAT ATA GAG ATT AAT GAA    722
Lys Gln Pro Asn Leu Thr Arg Thr Val Glu Asn Ile Glu Ile Asn Glu
        200             205             210

GAG GAT AAT GAG ATA AGT ATG TTG CAA GAA AAA GAG AGA TTT CAA        770
Glu Asp Asn Glu Ile Ser Met Leu Gln Glu Lys Glu Arg Phe Gln
215             220             225

GAA GTG TAA TTGTGGCGTG TATCAACACT GTTGCTTTCG TACATTGGGT GGTTCTAGA  828
Glu Val
```

PORCINE STEM CELL FACTOR VARIENTS AND RECOMBINANT CELLS EXPRESSING SUCH POLYPEPTIDES

This application claims the benefit of priority of U.S. Provisional Application Serial No. 60/055,735, filed Aug. 13. 1997.

BACKGROUND OF THE INVENTION

Field of the Invention

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been identified as being variant porcine stem cell factors, and in particular membrane-bound stem cell factors, and still more particularly as being involved in stem cell, useful for supporting proliferation and growth of porcine bone marrow cells.

SUMMARY OF THE INVENTION

The present invention provides in one aspect a novel polypeptide which has been characterized as an active form of porcine stem cell factor cDNA gene sequence(PSCF) that omits exon 6. Preferably, the PSCF is a splice variant wherein exon 6 is omitted. More preferably, exon 6 is removed from the native full-length porcine stem cell factor and is omitted entirely or is replaced with a polynucleotide that encodes one or more amino acids.

In a preferred aspect the invention provides a PSCF encoded by a polynucleotide sequence corresponding to the full-length native porcine stem cell factor cDNA, but in which: (1) the first 70 nucleotides are removed, (2) exon 6 is excised (nucleotides 591 to 654) from the full polynucleotide sequence, (3) the excised exon 6 segment is replaced by a three-nucleotide segment encoding the amino acid "Gly", and (4) the fifteen-nucleotide C-terminal tail (nucleotides 938–952) is removed and replaced by the six-nucleotide segment 5'-TCTAGA-3' (SEQ ID NO: 11).

In accordance with another aspect of the present invention, there are provided novel PSCF polypeptides, as well as active fragments, analogs and derivatives thereof. In a preferred aspect the present invention provides novel membrane-bound PSCF polypeptides, wherein the polypeptide segment encoded by exon 6 is omitted or replaced by an inactive polypeptide segment. In another preferred aspect the present invention provides such novel PSCF polypeptides which are soluble PSCF polypeptides.

In accordance with another aspect of the present invention, there are provided isolated nucleic acid molecules encoding the polypeptides of the present invention including mRNAs, cDNAs, genomic DNAs as well as active analogs and fragments of such polypeptides.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said polypeptides.

In accordance with a further aspect of the invention, the polypeptide of the invention may be anchored to a cell's surface, and the modified cell, as a feeder cell for culturing porcine cells.

In accordance with yet a further aspect of the present invention, there is provided a process for utilizing such polypeptides for analyzing potential agonists to the polypeptides, Another process utilizes the polynucleotides to assay for compounds which bind said polynucleotides and would thus block expression of any products from said polynucleotides.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such polypeptides, or polynucleotides encoding such polypeptides, for purposes related to scientific research for example, to generate probes for identifying similar sequences which might encode similar polypeptides from other organisms by using certain regions, i.e., conserved sequence regions, of the nucleotide sequence.

In accordance with an aspect of the present invention, there are provided isolated nucleic acids (polynucleotides) which encode PSCF polypeptides, in which polynucleotides exon 6 has been removed, deactivated or replaced by an inactive portion (SEQ ID NO:8) as shown in FIG. 4, as well as said encoded mature PSCF polypeptide as shown in FIG. 4 (SEQ ID NO:9).

These and other aspects of the present invention should be apparent to those skilled in the art from the teachings herein.

Definitions

In order to facilitate understanding of the following description and examples which follow certain frequently occurring methods and/or terms will be described.

The term "gene" means the segment of DNA involved in producing a polypeptide chain; it includes regions preceding and following the coding region (leader and trailer) as well as intervening non-coding sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired polypeptide.

"Recombinant" polypeptides refer to polypeptides produced by recombinant DNA techniques; i. e., produced from cells transformed by an exogenous DNA construct encoding the desired polypeptide. "Synthetic" polypeptides are those prepared by chemical synthesis.

A DNA "coding sequence of" or a"nucleotide sequence encoding" a particular polypeptide, is a DNA sequence which is transcribed and translated into a polypeptide when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel or an agarose gel to isolate the desired fragment.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate group with an ATP in the presence of a kinase. A synthetic oligonucleotide will ligate to a fragment that has not been dephosphorylated.

"Ligation" refers to the process of forming phosphodiester bonds between two double stranded nucleic acid fragments (J. Sambrook et al., 1989, in Molecular Cloning. A Laboratory Manual, Cold Spring Harbor Laboratory, NY). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in Sambrook et al., Molecular Cloning: A Laboratory Manual, Cold Spring Harbor Laboratory, 1989.

"Porcine Stem Cell Factor" (PSCF) or "porcine steel factor" are terms that are used herein interchangeably. Also the corresponding mouse factors are discussed as being "mouse stem factor" (MSF) or "mouse steel factor". PSCF is also called factor, porcine mast cell growth factor and porcine c-kit ligand in the art. Each of the native steel factors (SFs) has a transmembrane polypeptide with a cytoplasmic domain and an extracellular domain. Soluble PSCF or MSF refer to a fragment cleaved from the extracellular domain at a specific proteolytic cleavage site (e.g. for soluble PSCF, amino acids 1–160. Membrane associated SF refers to both normal SF before it has been cleaved or the SF which has been altered so that proteolytic cleavage cannot take place. The PSCF may be either a soluble form as described in U.S. Pat. No. 5,589,582, or its equivalents, or may be a membrane-bound form, preferably bound on to the surface of a cell.

"Feeder cells" are cells which produce membrane-bound and/or soluble PSCF, preferably a fibroblast cell that is transformed to produce the PSCF, more preferably are transformed murine fibroblast cells, and even more preferably are murine fibroblast cells known as the STO cell line that have been transformed. Particularly, preferred feeder cells have the polypeptide according to the invention anchored to the surface of the cell. Such feeder cell lines may be referred to above and hereinafter as "STO5", "STO8", "STO12" or "STO18" cells. Feeder cells which produce murine stem cell factor MSCF may be referred to as STO cells (the STO cell line is a thioguanine/oubain resistant sub-line of SIM mouse fibroblasts, Virology 50:339 (1972); STO cells are described in U.S. Pat. No. 5,453,357). The full-length amino acid sequence for PSCF (SEQ ID NO:2) based on native cDNA (SEQ ID NO:1 and FIG. 1 attached hereto) is reported in Biology of Reproduction 50: 95–102 (1994), and active forms can be produced by transfecting cells with active fragments of the cDNA sequence which may have the polynucleotides encoding the leader sequence amino acids (−25 to −1) removed. Soluble forms preferably omit the polynucleotide transmembrane portion. Additionally, an active form of PSCF (as in the present invention) can be produced and utilized to transfect STO cells by removing exon 6 from the full length cDNA and substituting a polynucleotide segment that encodes one or more amino acids. Active forms of the PSCF of the present invention may also omit the C-terminal polypeptide segment corresponding to native polypeptide beginning with amino acid 217 (see, FIG. 1 or SEQ ID NO:2 for such C-terminal segment).

BRIEF DESCRIPTION OF THE FIGURES

The following drawings are illustrative of an embodiment of the invention and are not meant to limit the scope of the invention as encompassed by the claims.

FIG. 1 illustrates the full-length sequence for PSCF (SEQ ID NO:2) based on native cDNA (SEQ ID NO:1) as reported in Biology of Reproduction 50: 95–102 (1994).

FIG. 2 illustrates the polynucleotide sequence (SEQ ID NO: 5) encoding a soluble form of PSCF (SEQ ID NO: 10) from U.S. Pat. No. 5,589,582.

FIG. 4 illustrates the polynucleotide sequence (SEQ ID NO:8) encoding an active membrane-bound form of PSCF (SEQ ID NO:9) from which exon 6 has been been removed and replaced with a tri-nucleotide that encodes the amino acid "Gly" which is part of plasmid pPSCF.

DETAILED DESCRIPTION OF THE INVENTION

Figure 3:
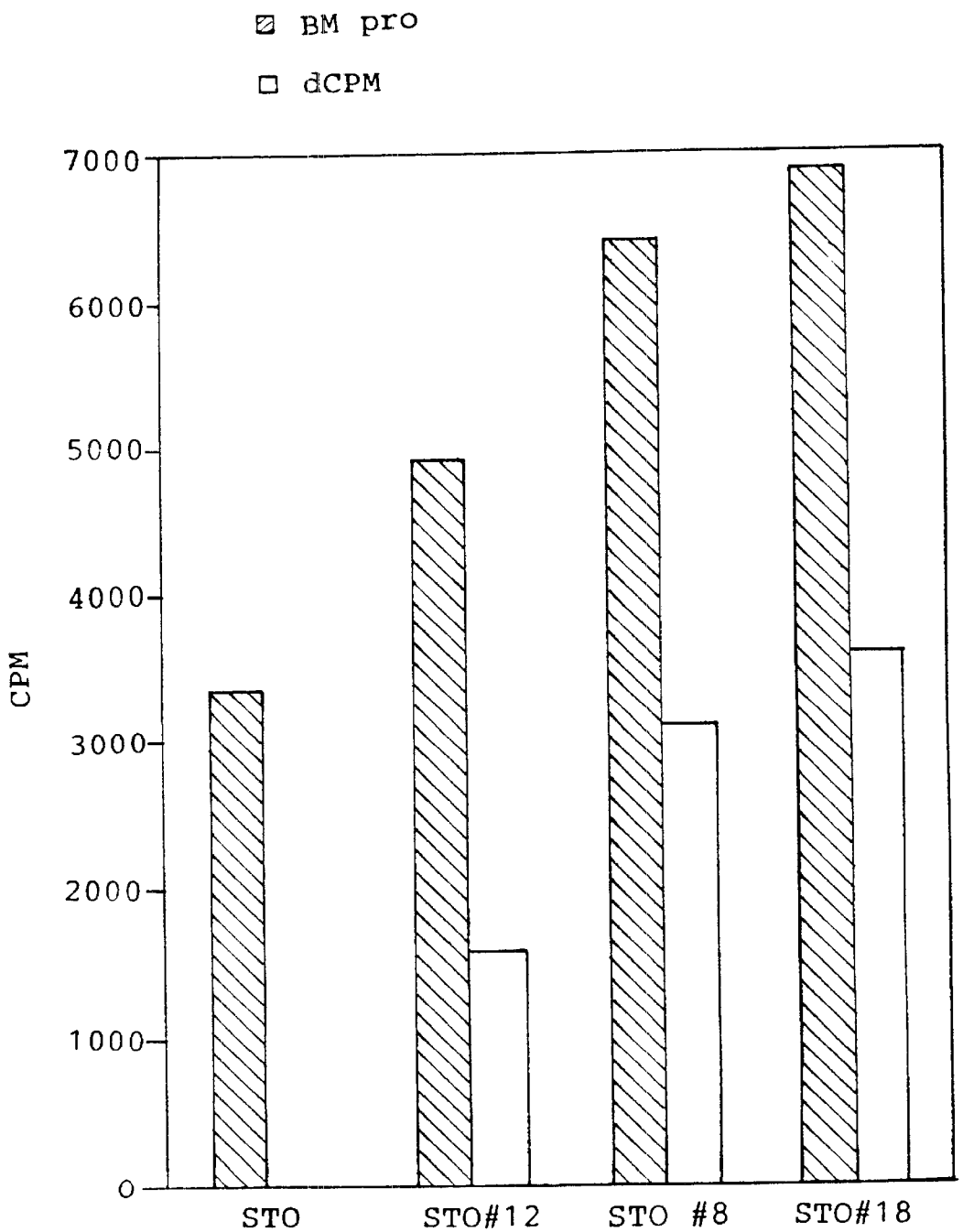
FIG. 3 shows a comparison of proliferation results for pig bone marrow cells cultured in the presence of STO cells as compared to STO cells transfected with the polynucleotide sequence that is set forth in FIG. 4. The proliferation results for pig bone marrow cells cultured in the presence of the transfected cells are significantly better than results with regular STO cells.

The polynucleotides of this invention coding for the polypeptides of this invention were originally recovered from a pig bone marrow stromal cells and modified to remove exon 6 as well as the C-terminal portion of the gene. Exon 6 was replaced with a tri-nucleotide "GGG" which encodes a "Gly" amino acid, but any polynucleotide encoding a polynucleotide sequence in phase with the remaining coding portion of the C-terminal portion of the PSCF native gene, which does not inactivate the resulting PSCF polypeptide may be used instead of the GGG tri-nucleotide.

The STO5, STO8, STO12 and STO18 are feeder cells according to the present invention wherein STO cells have been transfected with a polynucleotide which encodes a membrane-bound portion (or portions) of an active PSCF polypeptide.

As described above, to express the membrane form of porcine stem cell factor (PSCF) in the mouse fetal fibroblast feeder cell line STO and to provide STO5, STO8, STO12 and STO18 cell lines or the equivalent, the STO cells may be transfected with a portion of the cDNA encoding the PSCF gene. Alternatively, by eliminating the membrane-binding portion (portion corresponding to nucleotides 715 to 783 of the full length cDNA as shown in FIG. 1), the soluble form of PSCF may be produced by STO cells or the like transfected with the polynucleotide encoding the soluble PSCF polypeptide.

For example, STO8 cells are produced by transfecting STO cells with a polynucleotide sequence corresponding to the full-length cDNA in which: (1) the first 69 polynucleotides are removed, (2) exon 6 is excised (polynucleotides 592 to 654) from the full polynucleotide sequence, (3) the excised exon 6 segment is replaced by a three-nucleotide segment encoding the amino acid "Gly", and (4) the fifteen-nucleotide C-terminal tail (polynucleotides 938–952) is removed and replaced by the six-polynucleotide segment 5'-TCTAGA-3'.

Other active PSCF polynucleotides may be utilized. Particularly perferred are polynucleotides which are at least 80%, preferably 90%, and more preferably 95%, identical to a polynucleotide encoding a PSCF polypeptide corresponding to amino acids 1 to 196 of SEQ ID NO:9, or a corresponding soluble PSCF polypeptide from which the membrane-binding segment is omitted. The above mentioned documents that relate to various forms of PSCF are all incorporated herein by reference.

One means for isolating a polynucleotide encoding native PSCF or the PSCF according to the present invention is to utilize such polynucleotide or the polynucleotide according to the present invention (or one of their complements) as a probe. Thus, a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992) may be utilized. It is appreciated by one skilled in the art that the polynucleotides of SEQ ID NO:8, or fragments thereof (comprising at least 12 contiguous nucleotides), are particularly useful probes. Other particularly useful probes for this purpose are hybridizable fragments of the sequences of SEQ ID NOS: 1 or 5 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $NA_2EDTA$, 0.5% SDS, 10×Denhardt's, and 0.5 mg/mL polyriboadenylic acid. Approximately $2 \times 10^7$ cpm (specific activity $4–9 \times 10^8$ cpm/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8. 1 mM $Na_2EDTA$) containing 0.5% SDS, followed by a 30 minute wash in fresh 1×SET at Tm less 10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual*, 2d Ed., Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence is at least 70% and preferably at least 80%, and more preferably at least a 90%, and even more preferably or at least 95% identical to another DNA (RNA) sequence if there is at least 70% and preferably at least a 80% 90% or 95% identity, respectively, between the bases of the first sequence and the bases of the another sequence, when properly aligned with each other, for example when aligned by BLASTN.

The present invention relates to polynucleotides which differ from the reference polynucleotide in a manner such that the change or changes is/are silent change, in that the amino acid sequence encoded by the polynucleotide remains the same. The present invention also relates to nucleotide changes which result in amino acid substitutions, additions, deletions fusions and truncations in the polypeptide encoded by the reference polynucleotide. In a preferred aspect of the invention these polypeptides retain the same biological action as the polypeptide encoded by the reference polynucleotide.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encode the mature polypeptides (mature polypeptide may exclude the leader sequence and may optionally have an N-terminal methionine group such as when produced by an *E. coli* host cell or other prokaryotic host cell) and may be identical to the coding sequence shown in FIG. 4, (SEQ ID NOS:8) or may be a different coding sequence which coding sequence, as a result of the redundancy or degeneracy of the genetic code, encodes the same mature polypeptides as does the DNA of FIG. 4, (SEQ ID NOS:9, without the leader sequence –25 to –1, which may or may not be replaced with an N-terminal methionine group).

The polynucleotides which encode each of the mature polypeptide (SEQ ID NOS:8 absent the leader sequence –25 to –1) may include, but each is not limited to: only the coding sequence for the mature polypeptide; the coding sequence for the mature polypeptide and additional coding sequence such as a leader sequence or a propolypeptide sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequences.

The present invention further relates to variants of the hereinabove described polynucleotides which encode for fragments, analogs and derivatives of the polypeptides having the deduced amino acid sequences of FIG. 4 (SEQ ID NO:9).

The variant in the non-exon 6 portion of the polynucleotide may be a naturally occurring allelic variant of the polynucleotide or a non-naturally occurring variant of the polynucleotide. Of course the variant in its portion that replaces exon 6 may be varied in any manner which does not deactivate the overall polypeptide. In particular, polynucleotide sequences that encode relatively neutral polpeptides that are not capable of two or three-dimensional cross-bonding, e.g., sulfide bonding, are preferred.

Thus, the present invention includes polynucleotides encoding the same mature polypeptides as shown in FIG. 4 (absent the leader sequence), as well as variants of such polynucleotides which variants encode for a fragment, derivative or analog of the polypeptide of FIG. 4. Such nucleotide variants include deletion variants, substitution variants and addition or insertion variants.

As hereinabove indicated, the polynucleotides may have a coding sequence which is a naturally occurring allelic variant of the coding sequence shown in FIG. 4 (with regard to the non-exon 6 portions). As known in the art, an allelic variant is an alternate form of a polynucleotide sequence which may have a substitution, deletion or addition of one or more nucleotides, which does not substantially alter the function of the encoded polypeptide. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence identity to the gene. Probes of this type preferably have at least 10, preferably at least 15, and even more preferably at least 30 bases and may contain, for example, at least 50 or more bases. In fact, probes of this type having at least up to 150 bases or greater may also be utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides, having a sequence complementary to that of the gene or portion of the gene sequences of the present invention are used to screen a library of genomic DNA to determine which members of the library the probe hybridizes to in a complementary sense, have an identity as described above.

It is also appreciated that such probes can be and are preferably labeled with an analytically detectable reagent to facilitate identification of the probe. Useful reagents include but are not limited to radioactivity, fluorescent dyes or polypeptides capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptides encoded by the DNA of FIGS. 1A–D and 2A–E, respectively. In referring to identity in the case of hybridization, as known in the art, such identity refers to complementarity of polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotide of SEQ ID NO:8, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the polypeptide of SEQ ID NO:9, as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The present invention further relates to polypeptides which have the deduced amino acid sequence of FIG. 4, (SEQ ID NO:9) as well as fragments, analogs and derivatives of such polypeptides.

The terms "fragment," "derivative" and "analog" when referring to each of the polypeptides of FIG. 4, respectively, (SEQ ID NO:9, respectively) mean a polypeptide which retains essentially the same biological function or activity as such polypeptide. Thus, an analog includes a propolypeptide which can be activated by cleavage of the propolypeptide portion to produce an active mature polypeptide.

Furthermore, regardless of the absence or presence of biological PSCF activity, all of the polypeptides encoded by polynucleotides of the present invention having at least 70% polynucleotide sequence identity to the polynucleotide of SEQ ID NO:8 in the non-exon 6 portions, preferably at least 80% identity, more preferably at least 85% identical, even more preferably at least 90% identical, even further more preferably at least 95% identical and most preferably at least 97% identical. (or the complement polynucleotide) are useful as marker polypeptides. Such polypeptides can be utilized to produce antibodies against themselves (such as monoclonal antibodies) which can be utilized to detect or isolate such polypeptides. Thus, the successfully insertion of a construct comprising such polynucleotides into a host cell can be detected by utilizing such antibodies to assay for the presence of the polypeptide. Also, higher producing cell lines can be thus identified.

The polypeptides of the present invention may be a recombinant polypeptide and may comprise portions of a natural polypeptide or a synthetic polypeptide, but it is preferably a recombinant polypeptide.

The fragment, derivative or analog of the polypeptide of FIG. 4 (SEQ ID NO:9) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a propolypeptide sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:9 (in particular the mature polypeptides) as well as polypeptides which in the non-exon 6 derived portions have at least 70% similarity (preferably at least 70% identity) to the polypeptide of SEQ ID NO:9, more preferably at least 80% identity, even more preferably at least 85% identity, and further more preferably at least 90% similarity (more preferably at least 90% identity) to the polypeptide of SEQ ID NO:9, and still more preferably at least 95% similarity (still more preferably at least 95% identity) to the polypeptide of SEQ ID NO:9 with respect to the non-exon 6 derived portions, and also include portions of such polypeptides with such portion of the polypeptide generally containing at least 30 amino acids and more preferably at least 50 amino acids and most preferably at least up to 150 amino acids, or more. The mature polypeptides according to the invention may comprise or omit an N-terminal methionine amino acid residue.

As known in the art "similarity" between two polypeptides is determined by comparing the amino acid sequence and its conserved amino acid substitutes of one polypeptide to the sequence of a second polypeptide. The definition of 70% similarity would include a 70 amino acid sequence fragment of a 100 amino acid sequence, for example, or a 70 amino acid sequence obtained by sequentially or randomly deleting 30 amino acids from the 100 amino acid sequence.

A variant, i.e. a "fragment", "analog" or "derivative" polypeptide, and reference polypeptide may differ in amino acid sequence by one or more substitutions, additions, deletions. fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of protiens of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan. Preferred are host cells are to whose surface the polypeptide becomes bound or anchored.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli.$ The vector containing the appropriate DNA sequence as hereinabove described, as well as an appropriate promoter or control sequence, may be employed to transform an appropriate host to permit the host to express the polypeptide.

As representative examples of appropriate hosts, there may be mentioned: bacterial cells, such as $E.\ coli.$ Streptomyces, *Bacillus subtilis*; fungal cells, such as yeast; insect cells such as Dirosophila S2 and Spodoptera Sf9; animal cells such as CHO, COS or Bowes melanoma; adenoviruses; plant cells, etc. Preferred host cells are fibroblast cells from any species, preferably murine or porcine fibroblast cells, particularly preferred fibroblast are murine fibroblast cells and even more preferred are cells from the murine STO cell line. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukarvotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection. DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the polypeptides of the invention can be synthetically produced by conventional peptide synthesizers.

Mature polypeptides can be expressed in mammalian cells, yeast, bacteria, or other cells under the control of appropriate promoters. Depending upon the expression host a mature polypeptide may or may not contain an N-terminal methionine. Cell-free translation systems can also be employed to produce such polypeptides using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock polypeptides, among others. The heterologous structural sequence is assembled in appropriate phase with translation initiation and termination sequences, and preferably, a leader sequence capable of directing secretion of translated polypeptide. Optionally, the heterologous sequence can encode a fusion polypeptide including an N-terminal identification peptide imparting desired characteristics, e.g., stabilization or simplified purification of expressed recombinant product.

Useful expression vectors for bacterial use are constructed by inserting a structural DNA sequence encoding a desired polypeptide together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of polypeptides can be disrupted by any convenient method, including freeze-thaw cycling, sonication, mechanical disruption, or use of cell lysing agents, such methods are well known to those skilled in the art.

Various mammalian cell culture systems can also be employed to express recombinant polypeptide. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides according to the invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Polypeptide refolding steps can be used, as necessary, in completing configuration of the mature polypeptide. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may or may not also include an initial methionine amino acid residue.

Antibodies generated against a polypeptide corresponding to a sequence of the present invention can be obtained by direct injection of the respective polypeptide (or a portion of the polypeptide) into an animal or by administering the polypeptides to an animal, preferably a non-human. The antibody so obtained will then bind the respective polypeptide itself In this manner, even a sequence encoding only a fragment of the polypeptides can be used to generate antibodies binding the whole native polypeptides. Such antibodies can then be used to isolate the polypeptide from cells expressing that polypeptide and may also be useful as antimicrobials, or controls in assays to determine the efficacy of potential antimicrobials.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic polypeptide products of this invention. Also, transgenic mice may be used to express porcine antibodies to immunogenic polypeptide products of this invention.

Antibodies generated against a polypeptide of the present invention may be used in screening for similar polypeptides from other organisms and samples. Such screening techniques are known in the art, for example, one such screening assay is described in Sambrook and Maniatis. Molecular Cloning: A Laboratory Manual (2d Ed.), vol. 2: Section 8.49, Cold Spring Harbor Laboratory, 1989, which is hereby incorporated by reference in its entirety. Further, such antibodies are useful to detect the successful insertion of a transcript comprising the polynucleotide encoding the polypeptide which can be bound by such antibodies. Thus, the antibodies can be utilized to detect the "marker" polypeptide that is encoded by the polynucleotide inserted into the host cell.

The following non-limiting examples are provided merely to illustrate a preferred embodiment of the invention.

EXAMPLE 1

Preparation of STO8 Feeder Cells or Similar Feeder Cell Lines

A membrane-bound form of porcine stem cell factor is obtained by utilizing the STO cell line, which is a thioguanine/oubain resistant sub-line of SIM mouse fibroblasts, Virology 50:339 (1972); STO cells as described in U.S. Pat. No. 5,453,357). The STO cells are transfected with a membrane-bound portion which encodes an active PSCF polypeptide. The full-length sequence for PSCF (SEQ ID NO:2) based on native cDNA (SEQ ID NO:1) is reported in Biology of Reproduction 50: 95–102 (1994) (see also, FIG. 1. attached hereto), and an active form is produced by transfecting STO cells with active fragments of the cDNA coding sequence from which the polynucleotides encoding the leader sequence amino acids (−25 to −1) are removed and exon 6 polynucleotides are replaced with a trinucleotide fragment encoding the amino acid "Gly".

The following general procedure is followed. RNA is isolated from pig bone marrow stromal cells, RT-PCR is performed utilizing 1 μg total RNA in 6 μl $H_2O$ which is incubated at 65° C. for 3 minutes, then chilled on ice. Then added is 4 μl 5xRT buffer, 2 μl 0.1 M Dithiothreitol (DTT), 1 μl RNasin (Promega, Madison, Wis.), 2 μl 30 μM oligo $dT_{16}$, 2 μl dNTPs (10 mM each dATP, dTTP, dGTP, dCTP), 2 μl mg/ml BSA, 1 μl reverse transcriptase (Gibco Life Technologies, Baltimore, MD) and the reaction mixture is incubated at room temperature for 10 min., 42° C. for 60 min. 90° C. for 5 min. Then added is 1 μ RNase H (4 units, Gibco Life Technologies, Baltimore, Md.) and the reaction is incubated at 37° C. for 20 min, prior to Sephadex™ G-50 column chromatography to purify the cDNA product. The cDNA product is subjected to PCR using the oligonucleotides 5'MSFHindIII (5'GGT CAA GCT TCG CTG CCT TTC CTT ATG AAG AAG, SEQ ID NO: 3) and 3'MSFXbaI (5TCC ATC TAG AAC CAC CCA ATG TAC GAA AGC AAC, SEQ ID. NO: 4). SEQ ID NO: 1 contains a HindIII site and includes nucleotides 1–24 of SEQ ID NO: 3 (SEQ ID. NO:5 in this application) of U.S. Pat. No. 5,589,582). SEQ ID. NO: 4 contains an XbaI site and the reverse complement of nucleotides 915 through 935 of LO7786. The resulting PCR product is cleaved with HindIII and XbaI and cloned in pRcCMV (Invitrogen, Portland, Oreg.). The resulting plasmid is described as pSCFpRcCMV#2 and contains the full-length porcine cDNA for stem cell factor.

Xba and StuI are used to cleave pSCFpRcCMV#2 and a DNA fragment of approximately 250 bp (fragment 1) is isolated. ClaI and XbaI are also used to cleave pSCFpRc-CMV and a DNA fragment of approximately 6.2 Kb is isolated (fragment 2). Two oligonucleotides described as 5'SCFIk (SEQ ID NO: 6, ATCCATCGAT GCCTTCAAGG ATTTGGAGAT GGTGGCACCT AAAACTAGTG AAT-GTGTGAT TTCTTCAA) and 3'SCFlk (SEQ ID NO: 7 TCT GAGGCCTTCC TATTACTCT ACTGCTGTCA TTCCCTI=CAGGAGTTAA TGTTGAAGAA ATC) are synthesized. The oligonucleotides (1 μg (10 μg) of SEQ ID NO: 6 and 1 μg) 10 μl) SEQ ID NO: 7 are mixed with 3 μl 10xKlenow butter [SambrooK, 1989#1973] and incubated at 75° C. for 5 min, and then allowed to cool slowly. Afterwards 2 μl 2.5 mM each dXTP, 1.5 μl (7.5 unit) DNA polymerase Klenow fragment 3.5 μl H20 are added. After 30 min at 37° C., the reaction is heated at 70° C. for 10 min. The DNA fragment (fragment 3) is cleaved with ClaI and StuI. A three-way ligation is then performed with the DNA fragments 1,2 and 3. A resulting plasmid pPSCF is identified to have the correct sequence, shown in FIG. 4 (SEQ ID NO: 8 encoding amino acid sequence SEQ ID. NO: 9). The plasmid does not contain exon 6 and therefore is a form of SCF that is ordinarily expressed preferentially as a membrane bound form.

STO cells are electroporated according to the BIORAD (Hercules, Calif.) instructions for use of the Gene Pulses® Electroprotocols, using PvuI linerized pPSCF. Cells are selected for growth in G418 (500 μg/ml) and analyzed for the expression of the modified PSCF, using RT-PCR from RNA isolated from G418 resistant clones. Examples of STO cell lines that are successfully transfected with the polynucleotides of the above plasmid are designated as cell lines STO5, STO8, STO12 and STO18.

Cells (STO (control expressing murine membrane SCF), STO8, STO12 and STO18) are plated into 96 well flat bottom plates in Iscove's Modified Dulbecco's Media containing 10% heat-inactivated fetal bovine serum. Prior to the addition of bone marrow cells, the plates are irradiated to prevent further proliferation of the STO, STO5. STO8, STO12, and STO18 cells. Bone marrow cells are added to the wells. After 2 days in culture, 1 microcurie of $^3$H-Tdr is added to each well, and the plates are harvested on day 3. Results are counts per minute (cpm) and expressed as a mean value of triplicate plates. FIG. 3 shows that each of the transfected STO cell lines supports the proliferation of pig bone marrow cells to a greater extent than the untransfected STO cell line. The proliferative response on the bone marrow cells of the transfected cells is similar to that observed with untransfected STO cells that were cultured in combination with of 100–200 μg soluble pig SCF (for example, as set forth in U.S. Pat. No. 5,589,582). (data not reported)

Numerous modifications and variations of the present invention are possible in light of the above teachings and, therefore, within the scope of the appended claims, the invention may be practiced otherwise than as particularly described.

What is claimed is:

1. A recombinant vector comprising a polynucleotide wherein said polynucleotide is DNA and said polynucleotide is selected from the group consisting of (a) a polynucleotide encoding a polypeptide comprising amino acids 1 to 196 of SEQ ID NO:9 and (b) the complement of (a).

2. A recombinant host cell comprising a polynucleotide wherein said polynucleotide is a DNA and said polynucleotide is selected from the group consisting of (a) a polynucleotide encoding a polypeptide comprising amino acids 1 to 196 of SEQ ID NO:9 and (b) the complement of (a).

3. A recombinant host cell according to claim 2, wherein said host cell is a murine or porcine fibroblast cell.

4. The recombinant host cell according to claim 3, wherein said host cell is a murine STO cell.

5. A recombinant host cell according to claim 2, wherein said host cell is an STO cell.

6. A recombinant host cell according to claim 2, wherein said host cell will produce the polypeptide encoded by said polynucleotide as a polypeptide anchored to its surface.

7. A method for producing a polypeptide comprising expressing from the recombinant cell of claim 2 the polypeptide encoded by said polynucleotide.

* * * * *

UNITED STATES PATENT AND TRADEMARK OFFICE
CERTIFICATE OF CORRECTION

PATENT NO. : 6,670,151 B1
DATED : December 30, 2003
INVENTOR(S) : Manfred Baetscher It is certified that error appears in the above-identified patent and that said Letters Patent is hereby corrected as shown below:

Title page,
Item [54], Title, delete "VARIENTS" and insert therefor -- VARIANTS --

Column 2,
Line 64, delete "accord" and insert therefor -- accordance --

Column 4,
Line 49, delete "a"

Column 6,
Line 8, delete "a"
Line 10, delete "a" and insert therefor -- an --
Line 12, delete "of the another" and insert therefor -- of another --

Column 10,
Line 49, delete "lac or tip" and insert therefor -- lac or trp --

Column 12,
Line 44, delete "Wis." and insert therefor -- WI --

Column 14,
Line 61, delete "=" and insert therefor -- TTTT --
Line 64, delete "butter" and insert therefor -- buffer --

Column 16,
Line 14, delete "with of" and insert therefor -- with --

Signed and Sealed this

Twenty-ninth Day of June, 2004

JON W. DUDAS
*Acting Director of the United States Patent and Trademark Office*

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 952 BASE PAIRS
      (B) TYPE: NUCLEIC ACID
      (C) STRANDEDNESS: SINGLE
      (D) TOPOLOGY: LINEAR (ii) MOLECULE TYPE: cDNA (xi) SEQUENCE DESCRIPTION: SEQ ID NO: 1:

```
GAGCTCCAGA ACAGGTAAAC GGAGTTGCCA CACCGCTGCC TGGGCTGGAT CACAGCGCTG        60

CCTTTCCTT ATG AAG AAG ACA CAA ACT TGG ATT ATC ACT TGC ATT TAT          108
           Met Lys Lys Thr Gln Thr Trp Ile Ile Thr Cys Ile Tyr
           -25              -20                  -15

CTT CAA CTG CTC CTA TTT AAT CCT CTC GTC AGA ACT CAA GGG ATC TGC        156
Leu Gln Leu Leu Leu Phe Asn Pro Leu Val Arg Thr Gln Gly Ile Cys
        -10                  -5                    1

AGG AAC CGT GTG ACT GAT GAT GTG AAA GAC GTT ACA AAA TTG GTG GCA        204
Arg Asn Arg Val Thr Asp Asp Val Lys Asp Val Thr Lys Leu Val Ala
  5                  10                  15                  20

AAT CTT CCA AAA GAC TAT AAG ATA ACC CTC AAA TAT GTC CCC GGG ATG        252
Asn Leu Pro Lys Asp Tyr Lys Ile Thr Leu Lys Tyr Val Pro Gly Met
              25                  30                  35

GAC GTT TTG CCT AGT CAT TGT TGG ATA AGC GAA ATG GTG GAA CAA CTG        300
Asp Val Leu Pro Ser His Cys Trp Ile Ser Glu Met Val Glu Gln Leu
          40                  45                  50

TCA GTC AGC TTG ACT GAT CTT CTG GAC AAG TTT TCC AAT ATT TCT GAA        348
Ser Val Ser Leu Thr Asp Leu Leu Asp Lys Phe Ser Asn Ile Ser Glu
      55                  60                  65

GGC TTG AGT AAT TAT TCT ATC ATA GAC AAA CTT GTG AAA ATT GTT GAT        396
Gly Leu Ser Asn Tyr Ser Ile Ile Asp Lys Leu Val Lys Ile Val Asp
    70                  75                  80

GAC CTC GTG GAA TGC ATG GAA GAA CAC TCA TTT GAG AAT GTA AGA AAA        444
Asp Leu Val Glu Cys Met Glu Glu His Ser Phe Glu Asn Val Arg Lys
```

-continued

```
               85                  90                  95                 100
TCA TCT AAG AGC CCA GAA CCC AGG CTG TTT ACT CCT GAA AAA TTC TTT              492
Ser Ser Lys Ser Pro Glu Pro Arg Leu Phe Thr Pro Glu Lys Phe Phe
                        105                 110                 115

GGG ATT TTT AAT AGA TCC ATC GAT GCC TTC AAG GAT TTG GAG ATG GTG              540
Gly Ile Phe Asn Arg Ser Ile Asp Ala Phe Lys Asp Leu Glu Met Val
                        120                 125                 130

GCA CCT AAA ACT AGT GAA TGT GTG ATT TCT TCA ACA TTA ACT CCT GAA              588
Ala Pro Lys Thr Ser Glu Cys Val Ile Ser Ser Thr Leu Thr Pro Glu
                        135                 140                 145

AAA GAT TCC AGA GTC AGT GTC ACA AAA CCA TTT ATG TTA CCC CCT GTT              636
Lys Asp Ser Arg Val Ser Val Thr Lys Pro Phe Met Leu Pro Pro Val
            150                 155                 160

GCA GCC AGC TCC CTT AGG AAT GAC AGC AGT AGC AGT AAT AGG AAA GCC              684
Ala Ala Ser Ser Leu Arg Asn Asp Ser Ser Ser Ser Asn Arg Lys Ala
165                 170                 175                 180

TCA GAT TCG ATT GAA GAC TCC AGC CTC CAG TGG GCA GCG GTA GCA TTG              732
Ser Asp Ser Ile Glu Asp Ser Ser Leu Gln Trp Ala Ala Val Ala Leu
                        185                 190                 195

CCA GCA TTC TTC TCT CTT GTG ATT GGG TTT GCT TTT GGA GCC TTA TAC              780
Pro Ala Phe Phe Ser Leu Val Ile Gly Phe Ala Phe Gly Ala Leu Tyr
                        200                 205                 210

TGG AAG AAG AAA CAA CCA AAC CTT ACA AGG ACA GTG GAA AAT ATA GAG              828
Trp Lys Lys Lys Gln Pro Asn Leu Thr Arg Thr Val Glu Asn Ile Glu
            215                 220                 225

ATT AAT GAA GAG GAT AAT GAG ATA AGT ATG TTG CAA GAA AAA GAG AGA              876
Ile Asn Glu Glu Asp Asn Glu Ile Ser Met Leu Gln Glu Lys Glu Arg
            230                 235                 240

GAG TTT CAA GAA GTG TAA TTGTGGCGTG TATCAACACT GTTGCTTTCG TACATTGGT           934
Glu Phe Gln Glu Val
245

GGTAACAGTT GATGTTTG                                                          952
```

(2) INFORMATION FOR SEQ ID NO: 2:

(i) SEQUENCE CHARACTERISTICS:
        (A) LENGTH: 274 AMINO ACIDS
        (B) TYPE: AMINO ACID
        (C) STRANDEDNESS: <Unknown>
        (D) TOPOLOGY: LINEAR (ii) MOLECULE TYPE: PROTEIN (xi) SEQUENCE DESCRIPTION: SEQ ID NO: 2:

```
Met Lys Lys Thr Gln Thr Trp Ile Ile Thr Cys Ile Tyr Leu Gln
 -25                 -20                 -15

Leu Leu Leu Phe Asn Pro Leu Val Arg Thr Gln Gly Ile Cys Arg
-10                  -5                   1                   5

Asn Arg Val Thr Asp Asp Val Lys Asp Val Thr Lys Leu Val Ala
             10                  15                  20

Asn Leu Pro Lys Asp Tyr Lys Ile Thr Leu Lys Tyr Val Pro Gly
             25                  30                  35

Met Asp Val Leu Pro Ser His Cys Trp Ile Ser Glu Met Val Glu
             40                  45                  50

Gln Leu Ser Val Ser Leu Thr Asp Leu Leu Asp Lys Phe Ser Asn
             55                  60                  65

Ile Ser Glu Gly Leu Ser Asn Tyr Ser Ile Ile Asp Lys Leu Val
             70                  75                  80

Lys Ile Val Asp Asp Leu Val Glu Cys Met Glu Glu His Ser Phe
```

|          |          |          |
|----------|----------|----------|
| 85       | 90       | 95       |

Glu Asn Val Arg Lys Ser Ser Lys Ser Pro Glu Pro Arg Leu Phe
                100                 105                 110

Thr Pro Glu Lys Phe Phe Gly Ile Phe Asn Arg Ser Ile Asp Ala
                115                 120                 125

Phe Lys Asp Leu Glu Met Val Ala Pro Lys Thr Ser Glu Cys Val
                130                 135                 140

Ile Ser Ser Thr Leu Thr Pro Glu Lys Asp Ser Arg Val Ser Val
                145                 150                 155

Thr Lys Pro Phe Met Leu Pro Pro Val Ala Ala Ser Ser Leu Arg
                160                 165                 170

Asn Asp Ser Ser Ser Asn Arg Lys Ala Ser Asp Ser Ile Glu
                175                 180                 185

Asp Ser Ser Leu Gln Trp Ala Ala Val Ala Leu Pro Ala Phe Phe
                190                 195                 200

Ser Leu Val Ile Gly Phe Ala Phe Gly Ala Leu Tyr Trp Lys Lys
                205                 210                 215

Lys Gln Pro Asn Leu Thr Arg Thr Val Glu Asn Ile Gln Ile Asn
                220                 225                 230

Glu Glu Asp Asn Glu Ile Ser Met Leu Gln Glu Lys Glu Arg Glu
                235                 240                 245

Phe Gln Glu Val (2) INFORMATION FOR SEQ ID NO: 3:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO: 3:

GGTCAAGCTT CGCTGCCTTT CCTTATGAAG AAG                              33

(2) INFORMATION FOR SEQ ID NO: 4:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO: 4:

TCCATCTAGA ACCACCCAAT GTACGAAAGC AAC                              33

(2) INFORMATION FOR SEQ ID NO: 5:

(i) SEQUENCE CHARACTERISTICS:
        (A) LENGTH: 633 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO: 5:

GCGCT GCCTTTCCTT    15

```
ATG AAG AAG ACA CAA ACT TGG ATT ATC ACT TGC ATT TAT CTT CAA CTG        63
Met Lys Lys Thr Gln Thr Trp Ile Ile Thr Cys Ile Tyr Leu Gln Leu
-25             -20                 -15                 -10

CTC CTA TTT AAT CCT CTC GTC AGA ACT CAA GGG ATC TGC AGG AAC CGT       111
Leu Leu Phe Asn Pro Leu Val Arg Thr Gln Gly Ile Cys Arg Asn Arg
            -5                   1                   5

GTG ACT GAT GAT GTG AAA GAC GTT ACA AAA TTG GTG GCA AAT CTT CCA       159
Val Thr Asp Asp Val Lys Asp Val Thr Lys Leu Val Ala Asn Leu Pro
         10                  15                  20

AAA GAC TAT AAG ATA ACC CTC AAA TAT GTC CCC GGG ATG GAC GTT TTG       207
Lys Asp Tyr Lys Ile Thr Leu Lys Tyr Val Pro Gly Met Asp Val Leu
     25                  30                  35

CCT AGT CAT TGT TGG ATA AGC GAA ATG GTG GAA CAA CTG TCA GTC AGC       255
Pro Ser His Cys Trp Ile Ser Glu Met Val Glu Gln Leu Ser Val Ser
 40                  45                  50                  55

TTG ACT GAT CTT CTG GAC AAG TTT TCC AAT ATT TCT GAA GGC TTG AGT       303
Leu Thr Asp Leu Leu Asp Lys Phe Ser Asn Ile Ser Glu Gly Leu Ser
             60                  65                  70

AAT TAT TCT ATC ATA GAC AAA CTT GTG AAA ATT GTT GAT GAC CTC GTG       351
Asn Tyr Ser Ile Ile Asp Lys Leu Val Lys Ile Val Asp Asp Leu Val
         75                  80                  85

GAA TGC ATG GAA GAA CAC TCA TTT GAG AAT GTA AGA AAA TCA TCT AAG       399
Glu Cys Met Glu Glu His Ser Phe Glu Asn Val Arg Lys Ser Ser Lys
     90                  95                 100

AGC CCA GAA CCC AGG CTG TTT ACT CCT GAA AAA TTC TTT GGG ATT TTT       447
Ser Pro Glu Pro Arg Leu Phe Thr Pro Glu Lys Phe Phe Gly Ile Phe
105                 110                 115

AAT AGA TCC ATC GAT GCC TTC AAG GAT TTG GAG ATG GTG GCA CCT AAA       495
Asn Arg Ser Ile Asp Ala Phe Lys Asp Leu Glu Met Val Ala Pro Lys
120                 125                 130                 135

ACT AGT GAA TGT GTG ATT TCT TCA ACA TTA ACT CCT GAA AAA GAT TCC       543
Thr Ser Glu Cys Val Ile Ser Ser Thr Leu Thr Pro Glu Lys Asp Ser
             140                 145                 150

AGA GTC AGT GTC ACA AAA CCA TTT ATG TTA CCC CCT GTT GCA GCC AGC       591
Arg Val Ser Val Thr Lys Pro Phe Met Leu Pro Pro Val Ala Ala Ser
         155                 160                 165

TCC CTT AGG AAT GAC AGC AGT AGC AGT AAT AGG AAA GCC TAA               633
Ser Leu Arg Asn Asp Ser Ser Ser Ser Asn Arg Lys Ala
     170                 175                 180
```

(2) INFORMATION FOR SEQ ID NO: 6:

(i) SEQUENCE CHARACTERISTICS:
        (A) LENGTH: 68 BASE PAIRS
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO: 6:

```
ATCCATCGAT GCCTTCAAGG ATTTGGAGAT GGTGGCACCT AAAACTAGTG AATGTGTGAT    60

TTCTTCAA                                                             68
```

(2) INFORMATION FOR SEQ ID NO: 7:

(i) SEQUENCE CHARACTERISTICS:
        (A) LENGTH: 65 BASE PAIRS
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO: 7:

```
TCTGAGGCCT TCCTATTACT CTACTGCTGT CATTCCCTTT TTCAGGAGTT AATGTTGAAG      60

AAATC                                                                  65
```

(2) INFORMATION FOR SEQ ID NO: 8:

(i) SEQUENCE CHARACTERISTICS:
        (A) LENGTH: 828 BASE PAIRS
        (B) TYPE: NUCLEIC ACID
        (C) STRANDEDNESS: SINGLE
        (D) TOPOLOGY: LINEAR (ii) MOLECULE TYPE: cDNA (xi) SEQUENCE DESCRIPTION: SEQ ID NO: 8:

```
CGCTGCCTTT CCTT ATG AAG AAG ACA CAA ACT TGG ATT ATC ACT TGC ATT         50
             Met Lys Lys Thr Gln Thr Trp Ile Ile Thr Cys Ile
             -25                 -20                 -15

TAT CTT CAA CTG CTC CTA TTT AAT CCT CTC GTC AGA ACT CAA GGG ATC         98
Tyr Leu Gln Leu Leu Leu Phe Asn Pro Leu Val Arg Thr Gln Gly Ile
        -10                  -5                   1

TGC AGG AAC CGT GTG ACT GAT GAT GTG AAA GAC GTT ACA AAA TTG GTG        146
Cys Arg Asn Arg Val Thr Asp Asp Val Lys Asp Val Thr Lys Leu Val
      5                  10                  15

GCA AAT CTT CCA AAA GAC TAT AAG ATA ACC CTC AAA TAT GTC CCC GGG        194
Ala Asn Leu Pro Lys Asp Tyr Lys Ile Thr Leu Lys Tyr Val Pro Gly
 20                  25                  30                  35

ATG GAC GTT TTG CCT AGT CAT TGT TGG ATA AGC GAA ATG GTG GAA CAA        242
Met Asp Val Leu Pro Ser His Cys Trp Ile Ser Glu Met Val Glu Gln
             40                  45                  50

CTG TCA GTC AGC TTG ACT GAT CTT CTG GAC AAG TTT TCC AAT ATT TCT        290
Leu Ser Val Ser Leu Thr Asp Leu Leu Asp Lys Phe Ser Asn Ile Ser
             55                  60                  65

GAA GGC TTG AGT AAT TAT TCT ATC ATA GAC AAA CTT GTG AAA ATT GTT        338
Glu Gly Leu Ser Asn Tyr Ser Ile Ile Asp Lys Leu Val Lys Ile Val
         70                  75                  80

GAT GAC CTC GTG GAA TGC ATG GAA GAA CAC TCA TTT GAG AAT GTA AGA        386
Asp Asp Leu Val Glu Cys Met Glu Glu His Ser Phe Glu Asn Val Arg
     85                  90                  95

AAA TCA TCT AAG AGC CCA GAA CCC AGG CTG TTT ACT CCT GAA AAA TTC        434
Lys Ser Ser Lys Ser Pro Glu Pro Arg Leu Phe Thr Pro Glu Lys Phe
100                 105                 110                 115

TTT GGG ATT TTT AAT AGA TCC ATC GAT GCC TTC AAG GAT TTG GAG ATG        482
Phe Gly Ile Phe Asn Arg Ser Ile Asp Ala Phe Lys Asp Leu Glu Met
             120                 125                 130

GTG GCA CCT AAA ACT AGT GAA TGT GTG ATT TCT TCA ACA TTA ACT CCT        530
Val Ala Pro Lys Thr Ser Glu Cys Val Ile Ser Ser Thr Leu Thr Pro
             135                 140                 145

GAA AAA GGG AAT GAC AGC AGT AGC AGT AAT AGG AAA GCC TCA GAT TCG        578
Glu Lys Gly Asn Asp Ser Ser Ser Ser Asn Arg Lys Ala Ser Asp Ser
             150                 155                 160

ATT GAA GAC TCC AGC CTC CAG TGG GCA GCG GTA GCA TTG CCA GCA TTC        626
Ile Glu Asp Ser Ser Leu Gln Trp Ala Ala Val Ala Leu Pro Ala Phe
             165                 170                 175

TTC TCT CTT GTG ATT GGG TTT GCT TTT GGA GCC TTA TAC TGG AAG AAG        674
Phe Ser Leu Val Ile Gly Phe Ala Phe Gly Ala Leu Tyr Trp Lys Lys
180                 185                 190                 195

AAA CAA CCA AAC CTT ACA AGG ACA GTG GAA AAT ATA GAG ATT AAT GAA        722
Lys Gln Pro Asn Leu Thr Arg Thr Val Glu Asn Ile Glu Ile Asn Glu
             200                 205                 210
```

```
GAG GAT AAT GAG ATA AGT ATG TTG CAA GAA AAA GAG AGA GAG TTT CAA    770
Glu Asp Asn Glu Ile Ser Met Leu Gln Glu Lys Glu Arg Glu Phe Gln
            215                 220                 225

GAA GTG TAA TTGTGGCGTG TATCAACACT GTTGCTTTCG TACATTGGGT GGTTCTAGA  828
Glu Val
```

(2) INFORMATION FOR SEQ ID NO: 9:

(i) SEQUENCE CHARACTERISTICS:
        (A) LENGTH: 254 AMINO ACIDS
        (B) TYPE: AMINO ACID
        (C) STRANDEDNESS: <Unknown>
        (D) TOPOLOGY: LINEAR (ii) MOLECULE TYPE: PROTEIN (xi) SEQUENCE DESCRIPTION: SEQ ID NO: 9:

```
Met Lys Lys Thr Gln Thr Trp Ile Ile Thr Cys Ile Tyr Leu Gln
-25                 -20                 -15

Leu Leu Leu Phe Asn Pro Leu Val Arg Thr Gln Gly Ile Cys Arg
-10              -5                   1                   5

Asn Arg Val Thr Asp Asp Val Lys Asp Val Thr Lys Leu Val Ala
                10                  15                  20

Asn Leu Pro Lys Asp Tyr Lys Ile Thr Leu Lys Tyr Val Pro Gly
                25                  30                  35

Met Asp Val Leu Pro Ser His Cys Trp Ile Ser Glu Met Val Glu
                40                  45                  50

Gln Leu Ser Val Ser Leu Thr Asp Leu Leu Asp Lys Phe Ser Asn
                55                  60                  65

Ile Ser Glu Gly Leu Ser Asn Tyr Ser Ile Ile Asp Lys Leu Val
                70                  75                  80

Lys Ile Val Asp Asp Leu Val Glu Cys Met Glu Glu His Ser Phe
                85                  90                  95

Glu Asn Val Arg Lys Ser Ser Lys Ser Pro Glu Pro Arg Leu Phe
                100                 105                 110

Thr Pro Glu Lys Phe Phe Gly Ile Phe Asn Arg Ser Ile Asp Ala
                115                 120                 125

Phe Lys Asp Leu Glu Met Val Ala Pro Lys Thr Ser Glu Cys Val
                130                 135                 140

Ile Ser Ser Thr Leu Thr Pro Glu Lys Gly Asn Asp Ser Ser Ser
                145                 150                 155

Ser Asn Arg Lys Ala Ser Asp Ser Ile Glu Asp Ser Ser Leu Gln
                160                 165                 170

Trp Ala Ala Val Ala Leu Pro Ala Phe Phe Ser Leu Val Ile Gly
                175                 180                 185

Phe Ala Phe Gly Ala Leu Tyr Trp Lys Lys Lys Gln Pro Asn Leu
                190                 195                 200

Thr Arg Thr Val Glu Asn Ile Gln Ile Asn Glu Glu Asp Asn Glu
                205                 210                 215

Ile Ser Met Leu Gln Glu Lys Glu Arg Glu Phe Gln Glu Val
                220                 225
```

(2) INFORMATION FOR SEQ ID NO: 10:

(i) SEQUENCE CHARACTERISTICS:
        (A) LENGTH: 205 AMINO ACIDS
        (B) TYPE: AMINO ACID
        (C) STRANDEDNESS: <Unknown>

```
        (D) TOPOLOGY: LINEAR (ii) MOLECULE TYPE: PROTEIN (xi) SEQUENCE DESCRIPTION: SEQ ID NO: 10:

Met Lys Lys Thr Gln Thr Trp Ile Ile Thr Cys Ile Tyr Leu Gln Leu
-25             -20                 -15                 -10

Leu Leu Phe Asn Pro Leu Val Arg Thr Gln Gly Ile Cys Arg Asn Arg
            -5                   1               5

Val Thr Asp Asp Val Lys Asp Val Thr Lys Leu Val Ala Asn Leu Pro
        10              15              20

Lys Asp Tyr Lys Ile Thr Leu Lys Tyr Val Pro Gly Met Asp Val Leu
    25              30              35

Pro Ser His Cys Trp Ile Ser Glu Met Val Glu Gln Leu Ser Val Ser
40              45              50              55

Leu Thr Asp Leu Leu Asp Lys Phe Ser Asn Ile Ser Glu Gly Leu Ser
            60              65              70

Asn Tyr Ser Ile Ile Asp Lys Leu Val Lys Ile Val Asp Asp Leu Val
            75              80              85

Glu Cys Met Glu Glu His Ser Phe Glu Asn Val Arg Lys Ser Ser Lys
            90              95              100

Ser Pro Glu Pro Arg Leu Phe Thr Pro Glu Lys Phe Phe Gly Ile Phe
105                 110             115

Asn Arg Ser Ile Asp Ala Phe Lys Asp Leu Glu Met Val Ala Pro Lys
120             125             130             135

Thr Ser Glu Cys Val Ile Ser Ser Thr Leu Thr Pro Glu Lys Asp Ser
            140             145             150

Arg Val Ser Val Thr Lys Pro Phe Met Leu Pro Pro Val Ala Ala Ser
            155             160             165

Ser Leu Arg Asn Asp Ser Ser Ser Asn Arg Lys Ala
            170             175             180

(2) INFORMATION FOR SEQ ID NO: 11:

(i) SEQUENCE CHARACTERISTICS:
        (A) LENGTH: 6 BASE PAIRS
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO: 11:

TCTAGA                                                          6
```